(12) United States Patent
Kim et al.

(10) Patent No.: US 10,226,413 B2
(45) Date of Patent: Mar. 12, 2019

(54) SOLUTION SOLUBILIZATION COMPOSITION OF INSOLUBLE MATERIAL AND METHOD FOR SOLUBILIZING INSOLUBLE MATERIAL USING SAME

(71) Applicants: Damy Chemical Co., Ltd., Seoul (KR); KOREA RESEARCH INSTITUTE OF BIOSCIENCE AND BIOTECHNOLOGY, Daejeon (KR)

(72) Inventors: Kwang-Nyeon Kim, Gyeonggi-do (KR); Ju-Hyun Son, Seoul (KR); Hee-Sik Kim, Daejeon (KR)

(73) Assignees: DAMY CHEMICAL CO., LTD., Seoul (KR); KOREA RESEARCH INSTITUTE OF BIOSCIENCE AND BIOTECH, Daejeon (KR)

( * ) Notice: Subject to any disclaimer, the term of this patent is extended or adjusted under 35 U.S.C. 154(b) by 70 days.

(21) Appl. No.: 15/033,021

(22) PCT Filed: Nov. 15, 2013

(86) PCT No.: PCT/KR2013/010372
§ 371 (c)(1),
(2) Date: Apr. 28, 2016

(87) PCT Pub. No.: WO2015/072602
PCT Pub. Date: May 21, 2015

(65) Prior Publication Data
US 2016/0250129 A1    Sep. 1, 2016

(51) Int. Cl.
| | | |
|---|---|---|
| *A61K 8/68* | (2006.01) | |
| *A61K 47/30* | (2006.01) | |
| *A61K 47/36* | (2006.01) | |
| *A61K 31/164* | (2006.01) | |
| *A61K 31/047* | (2006.01) | |
| *A61K 31/05* | (2006.01) | |
| *A61K 31/122* | (2006.01) | |
| *A61K 31/165* | (2006.01) | |
| *A61K 31/19* | (2006.01) | |
| *A61K 31/53* | (2006.01) | |
| *A61K 8/34* | (2006.01) | |
| *A61K 8/35* | (2006.01) | |
| *A61K 8/49* | (2006.01) | |
| *A61K 8/60* | (2006.01) | |
| *A61K 8/73* | (2006.01) | |
| *A61K 8/86* | (2006.01) | |
| *A61K 8/92* | (2006.01) | |
| *A61K 9/08* | (2006.01) | |
| *A61K 31/56* | (2006.01) | |
| *A61K 31/7048* | (2006.01) | |
| *A61K 47/10* | (2017.01) | |
| *A61K 47/26* | (2006.01) | |
| *A61K 47/44* | (2017.01) | |

(Continued)

(52) U.S. Cl.
CPC ............... *A61K 8/68* (2013.01); *A61K 8/345* (2013.01); *A61K 8/347* (2013.01); *A61K 8/35* (2013.01); *A61K 8/4966* (2013.01); *A61K 8/602* (2013.01); *A61K 8/73* (2013.01); *A61K 8/86* (2013.01); *A61K 8/922* (2013.01); *A61K 8/99* (2013.01); *A61K 9/08* (2013.01); *A61K 9/1075* (2013.01); *A61K 31/047* (2013.01); *A61K 31/05* (2013.01); *A61K 31/122* (2013.01); *A61K 31/164* (2013.01); *A61K 31/165* (2013.01); *A61K 31/19* (2013.01); *A61K 31/53* (2013.01); *A61K 31/56* (2013.01); *A61K 31/7048* (2013.01); *A61K 47/10* (2013.01); *A61K 47/26* (2013.01); *A61K 47/30* (2013.01); *A61K 47/36* (2013.01); *A61K 47/44* (2013.01); *A61Q 19/00* (2013.01); *A61K 2800/10* (2013.01); *A61K 2800/49* (2013.01)

(58) Field of Classification Search
CPC ............ A61K 2880/10; A61K 2800/49; A61K 31/047; A61K 31/05; A61K 31/122; A61K 31/164; A61K 31/165; A61K 31/19; A61K 31/53; A61K 31/56; A61K 31/7048; A61K 47/10; A61K 47/26; A61K 47/30; A61K 47/36; A61K 47/44; A61K 8/347; A61K 8/68; A61K 8/73; A61K 8/86; A61K 8/922; A61K 9/08; A61K 8/345; A61K 8/99; A61K 9/1075; A61Q 19/00
See application file for complete search history.

(56) References Cited

U.S. PATENT DOCUMENTS

| | | |
|---|---|---|
| 2009/0035417 A1 | 2/2009 | Kawahara et al. |
| 2009/0208576 A1 | 8/2009 | Gandhi et al. |
| 2010/0168405 A1 | 7/2010 | Suzuki et al. |

FOREIGN PATENT DOCUMENTS

| | | |
|---|---|---|
| JP | 2010018560 A | 1/2010 |
| KR | 1020090008307 A | 1/2009 |
| KR | 101247803 B1 | 4/2013 |

OTHER PUBLICATIONS

Pepi et al. FEMS Microbiol. Ecol. (2005) 53: 157-166.*

(Continued)

*Primary Examiner* — Susan M Hanley
(74) *Attorney, Agent, or Firm* — Christensen, Fonder, Dardi & Herbert PLLC; Peter S. Dardi, Ph.D.

(57) ABSTRACT

The present invention relates to a solution solubilization composition of an insoluble material and a method for solubilizing an insoluble material using the same, on the basis of the mechanism that a solution solubilization composition of an insoluble material comprising mannosylerythritol lipid, an insoluble material, a heteropolysaccharide, a surfactant and a polyol offsets the intermolecular interaction of a hydrophobic material without physical requirements.

18 Claims, 6 Drawing Sheets

(51) Int. Cl.
    *A61Q 19/00*     (2006.01)
    *A61K 9/107*     (2006.01)
    *A61K 8/99*     (2017.01)

(56) References Cited

OTHER PUBLICATIONS

Machine Translation of KR 1027803B downloaded from KIPO on Aug. 31, 2017.*

Kodali et al., "An Exopolysaccharide From a Probiotic: Biosynthesis Dynamics, Composition and Emulsifying Activity", Food Research International, 42:695-699 (2009).

Cirigliano et al., "Purification and Characterization of Liposan, a Bioemulsifier From Candida Lipolytica", Applied and Environmental Microbiology, 50(4):846-850 (1985).

* cited by examiner

SOLUTION SOLUBILIZATION COMPOSITION OF INSOLUBLE MATERIAL AND METHOD FOR SOLUBILIZING INSOLUBLE MATERIAL USING SAME

CROSS REFERENCE TO RELATED APPLICATIONS

This application is a national phase filing of PCT Application No. PCT/KR2013/010372to KIM et al., filed Nov. 15, 2013, entitled "Solution Solubilization Composition Of Insoluble Material And Method For Solubilizing Insoluble Material Using Same," which is incorporated herein by reference.

BACKGROUND OF THE INVENTION

1. Field of the Invention

The present invention relates to a composition for solubilizing a poorly soluble substance in water and a method for solubilizing a poorly soluble substance in water by using the composition.

2. Description of the Related Art

Methods for solubilizing poorly soluble substances in water are currently being developed by many researchers in the cosmetic and pharmaceutical industries. It is expected that such techniques for solubilizing poorly soluble substances will be further developed in the future because of their significant ripple effects in the industry.

Poorly soluble hydrophobic substances have few or no hydrophilic groups or have hydrophilic groups at positions where their molecular arrangements are disturbed. The strong intermolecular hydrophobic interactions result in the formation of molecular arrangements that make it difficult to solubilize the hydrophobic substances in water. Any deformation of the molecular arrangements of the hydrophobic substances may make the poorly soluble substances dispersible or soluble. Substances capable of inducing changes in molecular arrangement are called surfactants.

A wide variety of surfactants have proven their usefulness in the cosmetic and pharmaceutical industries. Techniques have been developed for producing nanoparticles of poorly soluble substances using synthetic and natural surfactants under physical conditions created by suitable devices, such as ultra-homogenizers. However, the conventional techniques have limitations in solubilizing poorly soluble substances at high concentrations and stabilizing the solubilized substances. Thus, there has been an increasing demand for the development of new natural soluble substances and new solubilization systems.

Ceramides are well known as poorly soluble substances in the cosmetic industry. Ceramides are representative structural components of the skin that reinforce the barrier function of the skin. Human skin possesses various ceramides. Ceramides exhibit strong hydrophobic interactions in the skin due to the presence of a relatively small number of hydrophilic groups. Such structural features allow ceramides to exhibit their inherent skin barrier functions of preventing moisture loss from the human body and blocking the ingress of harmful ingredients from the external environment through the skin. Therefore, the application of ceramides to cosmetics increases the moisturizing power of the cosmetics and greatly enhances the skin-protecting power of the cosmetics, contributing to a considerable improvement in the quality of the cosmetics.

However, currently commercially available ceramides tend to aggregate in cosmetic formulations owing to high hydrophobic interactions between their molecular chains and hence possess serious disadvantages in that they are precipitated as needle-like crystals.

Solubilization of hydrophobic poorly soluble substances, such as rutein, resveratrol, phylloquinone, ubiquinone, oleanolic acid, bis-ethylhexyloxyphenol triazine, astaxanthin, rutin, hesperidin, and chloramphenicol, is considered a very important technical task in the cosmetic and pharmaceutical industries. Development of techniques for the solubilization of these hydrophobic poorly soluble substances is a crucial factor in maximizing the efficacy of the active ingredients and improving the quality of final products. In view of this situation, a strong need exists to develop new solubilization techniques.

Many researchers have made efforts to solve the above problems based on self-aggregation techniques and solubilization techniques. Despite such efforts, these techniques can be used at very limited concentrations in the current state of the art.

In most of such solubilization systems, phospholipids (e.g., phosphatidylcholine (lecithin)) as natural surfactants are currently in use. However, phospholipids are irregular in structure and have characteristic hydrophobic groups, limiting their use as solubilization substances. Particularly, phospholipids per se cannot be formed into small particles and have a limitation in that their particle size can be reduced to the micrometer or nanometer level only under high pressure.

Thus, there is a need to develop solubilization systems capable of solubilizing and stabilizing hydrophobic poorly soluble substances. Furthermore, there is an urgent need for the development of new materials that can form hydrophobic poorly soluble substances into nanoparticles without the need for physical pressure.

SUMMARY OF THE INVENTION

The present invention has been made in an effort to solve the above problems, and it is an object of the present invention to provide a composition for solubilizing a poorly soluble substance in water and a method for solubilizing a poorly soluble substance in water by using the composition.

One aspect of the present invention provides a composition for solubilizing a poorly soluble substance in water, including (a) a mannosylerythritol lipid, (b) a heteropolysaccharide, (c) a surfactant, and (d) a polyol.

In the present invention, the composition may include 100 parts by weight of the mannosylerythritol lipid (a), 0.1 to 100 parts by weight of the heteropolysaccharide containing galactose, glucose, and mannose units (b), 10 to 4500 parts by weight of the surfactant (c), and 10 to 3000 parts by weight of the polyol (d).

In the present invention, the mannosylerythritol lipid (a) may be represented by Formula 1:

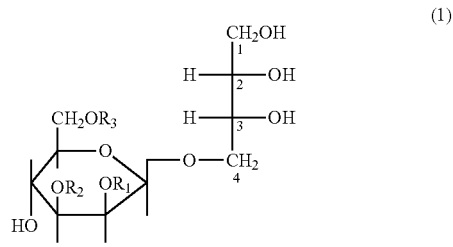

wherein $R_1$ and $R_2$ may be identical to or different from each other and are each independently a $C_6$-, $C_{12}$- or $C_{14}$-chain saturated or unsaturated fatty acid and $R_3$ is an acetyl group.

In the present invention, the heteropolysaccharide (b) may contain galactose, glucose, and mannose units in a molar ratio of 1-3:3-6:1-3.

In the present invention, the composition comprising the heteropolysaccharide containing galactose, glucose, and mannose units (b) may consist of a blend of polysaccharides with a first polysaccharide having a molecular weight of 50000 to 80000 daltons, a second polysaccharide having a molecular weight of 20000 to 50000 daltons, a third polysaccharide having a molecular weight of 5000 to 20000 daltons, a fourth polysaccharide having a molecular weight of 140000 to 160000 daltons, and a fifth polysaccharide having a molecular weight of 160000 to 180000 daltons.

In the present invention, the surfactant (c) may be selected from polyoxyethylene hydrogenated castor oil, Ceteareth, Ceteth, Glycereth, Laureth, Oleth, Polysorbates, Steareth, amino acid-fatty acid esters, polyoxyethylene stearate, and mixtures thereof.

In the present invention, the polyol (d) may be selected from butylene glycol, dipropylene glycol, propylene glycol, caprylyl glycol, decylene glycol, ethylene glycol, hexylene glycol, polyethylene glycol, glycerin, diglycerin, ethylhexylglycerin, polyglycerin, 1,6-hexanediol, 1,2-hexanediol, 1,2-octanediol, and mixtures thereof.

In the present invention, the poorly soluble substance may be any one that is used in a cosmetic or pharmaceutical composition and may be selected from ceramide, rutein, resveratrol, phylloquinone, ubiquinone, oleanolic acid, bis-ethylhexyloxyphenol methoxyphenyl triazine, astaxanthin, rutin, hesperidin, chloramphenicol, and mixtures thereof.

The present invention also provides a method for solubilizing a poorly soluble substance in water, including (i) sequentially mixing a mannosylerythritol lipid, a poorly soluble substance, a heteropolysaccharide, a surfactant, and a polyol and (ii) heating and stirring the mixture.

In the present invention, the mixture may include 100 parts by weight of the mannosylerythritol lipid, 2 to 4000 parts by weight of the poorly soluble substance, 0.1 to 100 parts by weight of the heteropolysaccharide containing galactose, glucose, and mannose units, 10 to 4500 parts by weight of the surfactant, and 10 to 3000 parts by weight of the polyol.

In the present invention, the mannosylerythritol lipid may be represented by Formula 1:

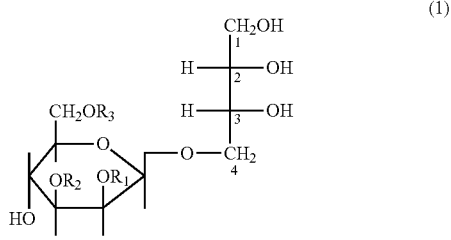

(1)

wherein $R_1$ and $R_2$ may be identical to or different from each other and are each independently a $C_6$-, $C_{12}$- or $C_{14}$-chain saturated or unsaturated fatty acid and $R_3$ is an acetyl group.

In the present invention, the heteropolysaccharide may contain galactose, glucose, and mannose units in a molar ratio of 1-3:3-6:1-3.

In the present invention, the heteropolysaccharide containing galactose, glucose, and mannose units may be produced from *Candida* sp.

In the present invention, heteropolysaccharides containing galactose, glucose, and mannose units may consist of a blend of polysaccharides with a first polysaccharide having a molecular weight of 50000 to 80000 daltons, a second polysaccharide having a molecular weight of 20000 to 50000 daltons, a third polysaccharide having a molecular weight of 5000 to 20000 daltons, a fourth polysaccharide having a molecular weight of 140000 to 160000 daltons, and a fifth polysaccharide having a molecular weight of 160000 to 180000 daltons.

In the present invention, the surfactant may be selected from polyoxyethylene hydrogenated castor oil, Ceteareth, Ceteth, Glycereth, Laureth, Oleth, Polysorbates, Steareth, amino acid-fatty acid esters, polyoxyethylene stearate, and mixtures thereof.

In the present invention, the polyol may be selected from butylene glycol, dipropylene glycol, propylene glycol, caprylyl glycol, decylene glycol, ethylene glycol, hexylene glycol, polyethylene glycol, glycerin, diglycerin, ethylhexylglycerin, polyglycerin, 1,6-hexanediol, 1,2-hexanediol, 1,2-octanediol, and mixtures thereof.

In the present invention, the poorly soluble substance may be any one that is used in a cosmetic or pharmaceutical composition and may be selected from ceramide, rutein, resveratrol, phylloquinone, ubiquinone, oleanolic acid, bis-ethylhexyloxyphenol methoxyphenyl triazine, astaxanthin, rutin, hesperidin, chloramphenicol, and mixtures thereof.

In the present invention, the heating temperature may be from 40 to 80° C.

The composition and the method of the present invention are effective in solubilizing poorly soluble substances that are known to have good activities but have limited large-scale applications.

In addition, the composition and the method of the present invention efficiently improve the solubilization of various kinds of poorly soluble substances, which have previously been difficult to solubilize, so that the effects of final products containing the substances can be maximized.

DETAILED DESCRIPTION OF THE INVENTION

Figure 1:
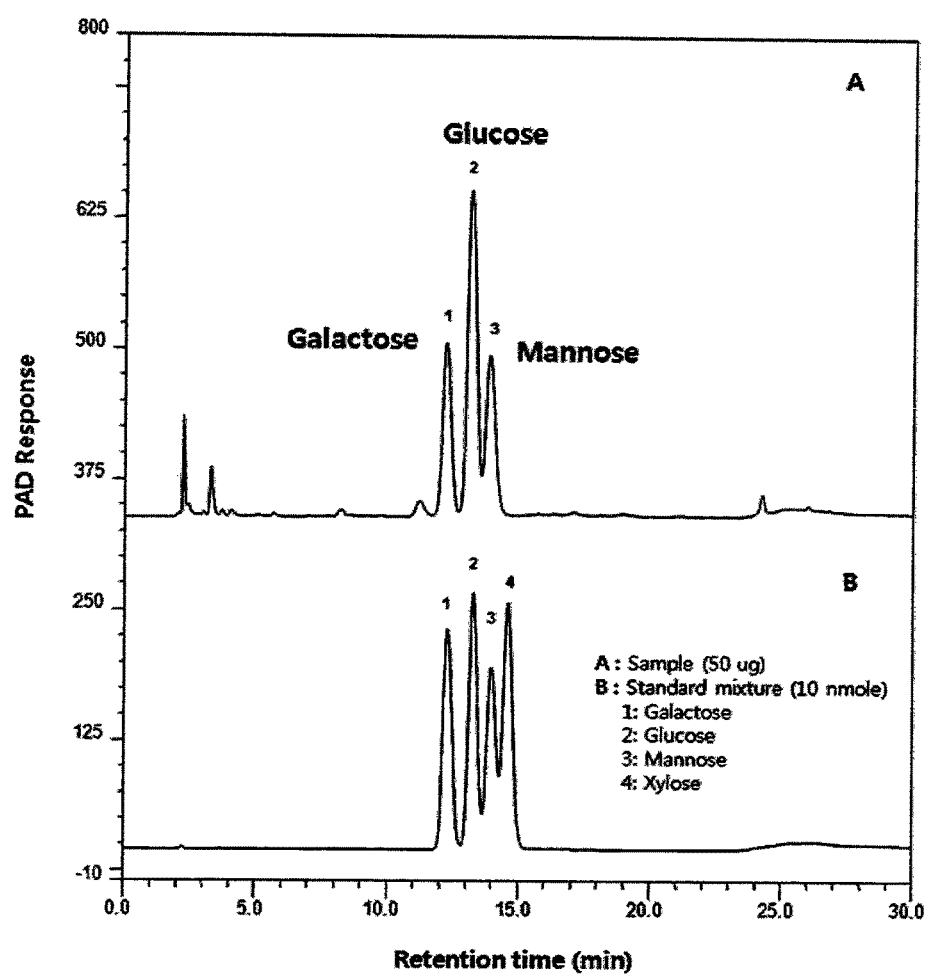
FIG. 1 shows a plot of IC-PAD analysis for the constituent monosaccharides of a heteropolysaccharide used in a composition according to one embodiment of the present invention (plot A) with a standard mixture for comparison (plot B).

A detailed description will be given of a composition for solubilizing a poorly soluble substance in water and a method for solubilizing a poorly soluble substance in water by using the composition.

Composition for Solubilizing Poorly Soluble Substance in Water

The composition of the present invention includes (a) a mannosylerythritol lipid, (b) a heteropolysaccharide comprising galactose, glucose, and mannose, (c) a surfactant, and (d) a polyol.

According to a preferred embodiment of the present invention, the mannosylerythritol lipid (a) is a kind of surfactant produced from *Candida* sp. SY16 (KCTC 8950P) and is a glycolipid surfactant in which a fatty acid is bound to mannosylerythritol.

The heteropolysaccharide (b) contains galactose, glucose, and mannose units and is produced from *Candida* sp. SY16 (KCTC 8950P). The heteropolysaccharide (b), together with the mannosylerythritol lipid, is mixed with a poorly soluble substance to induce rearrangement of the poorly soluble substance, thereby serving to solubilize the poorly soluble substance. The heteropolysaccharide contains large amounts of galactose, glucose, and mannose units and may contain small amounts of other monosaccharide units, such as rhamnose, arabinose, and xylose.

After the mannosylerythritol lipid and the heteropolysaccharide containing galactose, glucose, and mannose units solubilize a poorly soluble substance, the resulting solution becomes visually transparent. At this time, the micelle particles of the poorly soluble substance do not scatter incident visible light due to its smaller size than the cut-off wavelength of visible light. The micelle particles of the poorly soluble substance present in the composition of the present invention may be not larger than 50 nm, 30 nm or 20 nm in size.

After the mannosylerythritol lipid and the heteropolysaccharide containing galactose, glucose, and mannose units solubilize a poorly soluble substance, the particles of the poorly soluble substance remain unaggregated due to the repulsive force between the particles, achieving high dispersion stability. Zeta potential refers to the potential in a slip plane close to the interface between an immobile layer and a diffuse layer. Since the composition of the present invention and the particles of a poorly soluble substance have zeta potentials of the same polarity (i.e. both are either highly negatively or positively charged), they are not bound to each other, achieving high dispersion stability. The composition of the present invention and the particles of the poorly soluble substance may have absolute zeta potential values of at least 30 mV or 35 mV.

The composition of the present invention may include 100 parts by weight of the mannosylerythritol lipid (a), 0.1 to 100 parts by weight of the heteropolysaccharide containing galactose, glucose, and mannose units (b), 10 to 4500 parts by weight of the surfactant (c), and 10 to 3000 parts by weight of the polyol (d). When the components of the composition are within the content ranges defined above, the activity of a poorly soluble substance to be solubilized by the composition can be maximized and the stability thereof can be ensured.

The heteropolysaccharide containing galactose, glucose, and mannose units is preferably present in an amount of 0.5 to 100 parts by weight, more preferably 1 to 50 parts by weight, based on 100 parts by weight of the mannosylerythritol lipid. If the content of the heteropolysaccharide containing galactose, glucose, and mannose units is less than 0.1 parts by weight, the heteropolysaccharide together with the mannosylerythritol lipid cannot sufficiently solubilize a poorly soluble substance, making it difficult to expect its satisfactory effect. Further, the particles of the poorly soluble substance become larger, causing poor transparency of a final solubilization product. Meanwhile, the presence of the heteropolysaccharide containing galactose, glucose, and mannose units in an amount exceeding 100 parts by weight decreases the function of the mannosylerythritol lipid solubilizing a poorly soluble substance, leading to recrystallization of the poorly soluble substance.

If the content of the surfactant is less than 10 parts by weight, based on 100 parts by weight of the mannosylerythritol lipid, it does not support the main function of the mannosylerythritol lipid solubilizing a poorly soluble substance, and as a result, the size of the poorly soluble substance become larger, causing poor transparency of a final solubilization product. Meanwhile, the presence of the surfactant in an amount exceeding 4500 parts by weight decreases the function of the mannosylerythritol lipid solubilizing a poorly soluble substance, leading to recrystallization of the poorly soluble substance.

If the content of the polyol is less than 10 parts by weight, based on 100 parts by weight of the mannosylerythritol lipid, the stability maintenance of nanoparticles in an aqueous phase may be impaired. Meanwhile, the presence of the polyol in an amount exceeding 3000 parts by weight decreases the function of the mannosylerythritol lipid solubilizing a poorly soluble substance, leading to recrystallization of the poorly soluble substance.

In the present invention, the mannosylerythritol lipid (a) may be represented by Formula 1:

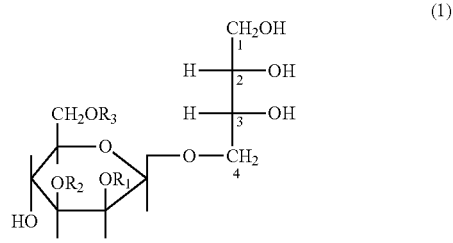

(1)

wherein $R_1$ and $R_2$ may be identical to or different from each other and are each independently a $C_6$-, $C_{12}$- or $C_{14}$-chain saturated or unsaturated fatty acid and $R_3$ is an acetyl group.

In the present invention, the heteropolysaccharide (b) may contain galactose, glucose, and mannose units in a molar ratio of about 1-3:3-6:1-3, most preferably 1:2:1.

In the present invention, composition comprising the heteropolysaccharide containing galactose, glucose, and mannose units (b) may consist of a blend of five different polysaccharides. The constituent polysaccharides may be a first polysaccharide having a molecular weight of 50000 to 80000 daltons, a second polysaccharide having a molecular weight of 20000 to 50000 daltons, a third polysaccharide having a molecular weight of 5000 to 20000 daltons, a fourth polysaccharide having a molecular weight of 140000 to 160000 daltons, and a fifth polysaccharide having a molecular weight of 160000 to 180000 daltons. Preferably, the first polysaccharide has a molecular weight of 65000 to 70000 daltons, the second polysaccharide has a molecular weight of 35000 to 40000 daltons, the third polysaccharide has a molecular weight of 5000 to 10000 daltons, the fourth polysaccharide has a molecular weight of 145000 to 150000 daltons, and the fifth polysaccharide has a molecular weight of 165000 to 170000 daltons.

In the present invention, the surfactant (c) is added separately from the mannosylerythritol lipid (a) and assists in the solubilization function of the mannosylerythritol lipid. The surfactant (c) is preferably selected from, but not limited to, polyoxyethylene hydrogenated castor oil, Ceteareth, Ceteth, Glycereth, Laureth, Oleth, Polysorbates, Steareth, amino acid-fatty acid esters, polyoxyethylene stearate, and mixtures thereof.

Like the surfactant (c), the polyol (d) is a material assisting in the solubilization function of the mannosylerythritol lipid. The polyol (d) is preferably selected from, but not limited to, butylene glycol, dipropylene glycol, propylene glycol, caprylyl glycol, decylene glycol, ethylene glycol, hexylene glycol, polyethylene glycol, glycerin, diglycerin, ethylhexylglycerin, polyglycerin, 1,6-hexanediol, 1,2-hexanediol, 1,2-octanediol, and mixtures thereof.

The composition of the present invention may be applied to the solubilization of a poorly soluble substance used in a cosmetic or pharmaceutical composition. The poorly soluble substance may be selected from, but not limited to, ceramide, rutein, resveratrol, phylloquinone, ubiquinone, oleanolic acid, bis-ethylhexyloxyphenol methoxyphenyl triazine, astaxanthin, rutin, hesperidin, chloramphenicol, and mixtures thereof.

Method for Solubilizing Poorly Soluble Substance in Water

The method of the present invention includes (i) sequentially mixing a mannosylerythritol lipid, a poorly soluble substance, a heteropolysaccharide, a surfactant, and a polyol and (ii) heating and stirring the mixture.

In the present invention, the mixture may include 100 parts by weight of the mannosylerythritol lipid, 2 to 4000 parts by weight of the poorly soluble substance, 0.1 to 100 parts by weight of the heteropolysaccharide containing galactose, glucose, and mannose units, 10 to 4500 parts by weight of the surfactant, and 10 to 3000 parts by weight of the polyol.

The kinds of the mannosylerythritol lipid, the heteropolysaccharide containing galactose, glucose, and mannose units, the surfactant, the polyol, and the poorly soluble substance used in the method of the present invention are the same as those described above.

Thus, the same descriptions as above will be omitted or briefly mentioned to avoid duplication.

According to the method of the present invention, in step (i), a mannosylerythritol lipid, a poorly soluble substance, a heteropolysaccharide containing galactose, glucose, and mannose units, a surfactant, and a polyol are sequentially mixed.

The mannosylerythritol lipid, the poorly soluble substance, the heteropolysaccharide containing galactose, glucose, and mannose units, the surfactant, and the polyol are sequentially mixed in the amounts described above. In this step, it is important to add the mannosylerythritol lipid, the hydrophobic poorly soluble substance, and the heteropolysaccharide containing galactose, glucose, and mannose units in this order. The amounts of the constituent materials in the mixture are important considerations in preparing a transparent solubilization product containing a high concentration of the poorly soluble substance.

In subsequent step (ii), the mixture is heated and stirred. The heating temperature is preferably from 40 to 80° C. If the heating temperature is lower than 40° C., the raw materials are not homogenized, deteriorating the ability of the composition to solubilize the poorly soluble substance. Meanwhile, if the heating temperature exceeds 80° C., the problems of discoloration and rancidity may arise.

The method of the present invention enables the preparation of a highly transparent solubilization product containing the poorly soluble substance at a high concentration of at least 15%.

The present invention will be explained in more detail with reference to the following examples. However, these examples are not intended to limit the scope of the invention.

EXPERIMENTAL EXAMPLE 1

Characterization of Polysaccharide Produced from *Candida* sp.

EXPERIMENTAL EXAMPLE 1-1

Measurement of Constituent Saccharides

50 μg of a sample of a heteropolysaccharide produced from *Candida* sp. and 10 nmole of a standard mixture were analyzed using ion chromatography/pulsed amperometric detection (IC/PAD) under the conditions shown in Table 1 and the results are shown in A and B of FIG. 1, respectively.

TABLE 1

| Analysis conditions | |
| --- | --- |
| Apparatus | CarboPac PA1 |
| Eluents | A: D.W. B: 200 mM NaOH |
| Eluent Flow Rate | 0.8 ml/min |
| Injection Volume | 10 μl |
| Temperature | Room Temperature |
| Detection | PAD (gold) |

From the results in Table 1, the heteropolysaccharide produced from *Candida* sp. was confirmed to contain large amounts of glucose, galactose, and mannose units in a molar ratio of about 2:1:1.

EXPERIMENTAL EXAMPLE 1-2

Molecular Weight Measurement

Figure 2:
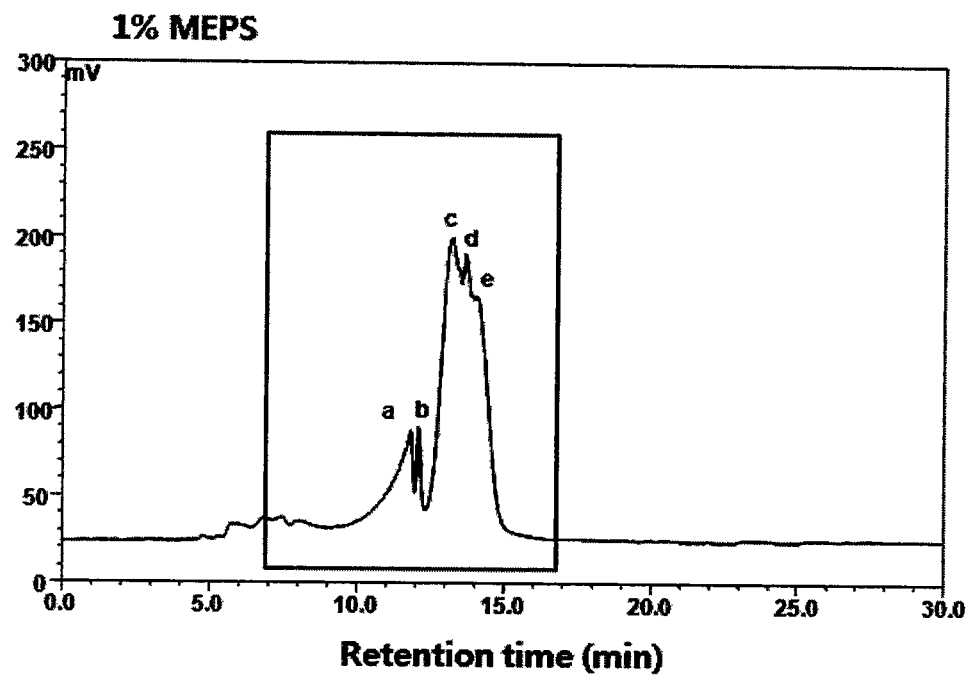
FIG. 2 shows the molecular weights of five constituent polysaccharides of a heteropolysaccharide used in a composition according to one embodiment of the present invention.
Figure 2:
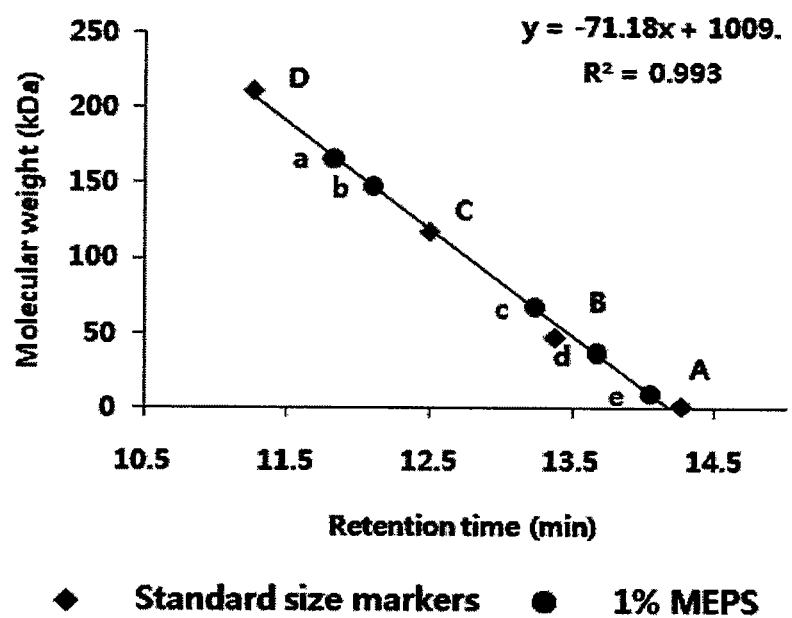

The molecular weight of the heteropolysaccharide produced from *Candida* sp. was measured by high performance liquid chromatography (HPLC) under the conditions shown in Table 2 and was compared with those of 0.1% standard pullulans (212000 Da, 118000 Da, 47300 Da, and 1320 Da). The results are shown in FIG. 2.

TABLE 2

Analysis conditions

| Apparatus | ShodexOhpak SB-805 HQ (300 × 8 mm) |
|---|---|
| Flow Rate | 0.8 ml/min |
| Injection Vol. | 10 μl |
| Temperature | 30° C. |
| Detector | ELSD |

As a result of the molecular weight measurement based on the series of standards (pullulans), the heteropolysaccharide produced from *Candida* sp. was confirmed to consist of five kinds of polysaccharides having different molecular weights of 9963 Da, 36229 Da, 67904 Da, 148054 Da, and 167059 Da.

EXAMPLE 1

Preparation of Solubilization Compositions Containing Different Amounts of the Heteropolysaccharide A ceramide, a mannosylerythritol lipid, and the heteropolysaccharide produced from *Candida* sp. were mixed in the amounts shown in Table 3. The mixture was stirred and heated to 80° C. to obtain a solution. The other components shown in Table 3 were sequentially added to the solution, heated to 80° C., stirred, and cooled to prepare a composition containing the poorly soluble substance.

TABLE 3

Compositions of Example 1

| Component (g) | Comparative Example 1-1 | Example 1-1 | 1-2 | 1-3 | 1-4 | 1-5 | 1-6 | 1-7 | 1-8 | 1-9 |
|---|---|---|---|---|---|---|---|---|---|---|
| Ceramide | 20 | 20 | 20 | 20 | 20 | 20 | 20 | 20 | 20 | 20 |
| Mannosylerythritol lipid | 25 | 25 | 25 | 25 | 25 | 25 | 25 | 25 | 25 | 25 |
| Polyoxyethylene (EO = 40) hydrogenated castor oil | 25 | 25 | 25 | 25 | 25 | 25 | 25 | 25 | 25 | 25 |
| Butylene glycol | 20 | 19.9 | 19.5 | 19 | 18 | 17 | 16 | 15 | 10 | 5 |
| Dipropylene glycol | 5 | 5 | 5 | 5 | 5 | 5 | 5 | 5 | 5 | 5 |
| Propylene glycol | 5 | 5 | 5 | 5 | 5 | 5 | 5 | 5 | 5 | 5 |
| Heteropolysaccharide | — | 0.1 | 0.5 | 1 | 2 | 3 | 4 | 5 | 10 | 15 |

EXAMPLE 2

Preparation of Solubilization Products Including the Solubilization Compositions of Example 1

As shown in Table 4, purified water was added to the compositions of Example 1, each of which included the excess ceramide, to prepare final products in which the ceramide was solubilized.

Specifically, 5 wt % of each composition prepared in Example 1 was heated to 80° C. and purified water at 80° C. was slowly added thereto with stirring to solubilize the ceramide. The ceramide content of the final solubilization product was 1.0 wt % because the composition including 20 wt % of the ceramide was used in an amount of 5 wt %.

TABLE 4

Composition of Example 2

| Component | Amount (wt %) |
|---|---|
| Ceramide-containing composition | 5 |
| Purified water | 95 |

EXPERIMENTAL EXAMPLE 2

Evaluation of Turbidities and Transmittances of the Compositions Prepared in Example 1

The transparency of the lotions (solubilization products) of Example 2, which were prepared using the ceramide-containing compositions of Example 1, was evaluated by the following methods.

(1) Turbidity Evaluation Method

The turbidity of each lotion was measured using a spectrophotometer at 620 nm. A high turbidity of a liquid indicates cloudiness of the liquid and a low turbidity of a liquid indicates high transparency of the liquid. The turbidity (optical density) of the lotion was measured in the range of 0.01-1.0.

(2) Transmittance Evaluation Method

The amount of light passing through each solution was measured. The transmittance (T, %) of the solution for light was calculated as follows. First, the measured absorbance was substituted into -log t=A (absorbance, O.D). Since t is always not greater than 1, the transmittance (T) was calculated and expressed in percentage by T (%)=t×100. The transmittance is between 1 and 100%. The higher the transmittance, the higher the transparency. The transmittance of purified water was defined as 100%. For example, if a sample has a transmittance of 40% for light, 60% of the light does not pass through the sample.

(3) Evaluation Results

Figure 3:
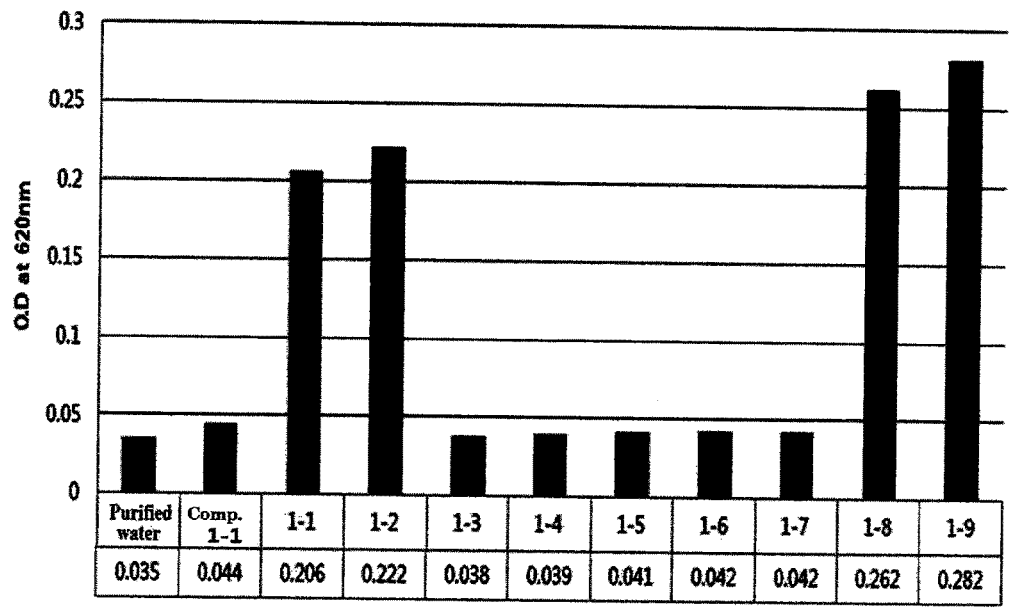
FIG. 3 shows the turbidity values of solubilization products containing different amounts of a heteropolysaccharide, which were prepared in Example 2.
Figure 4:
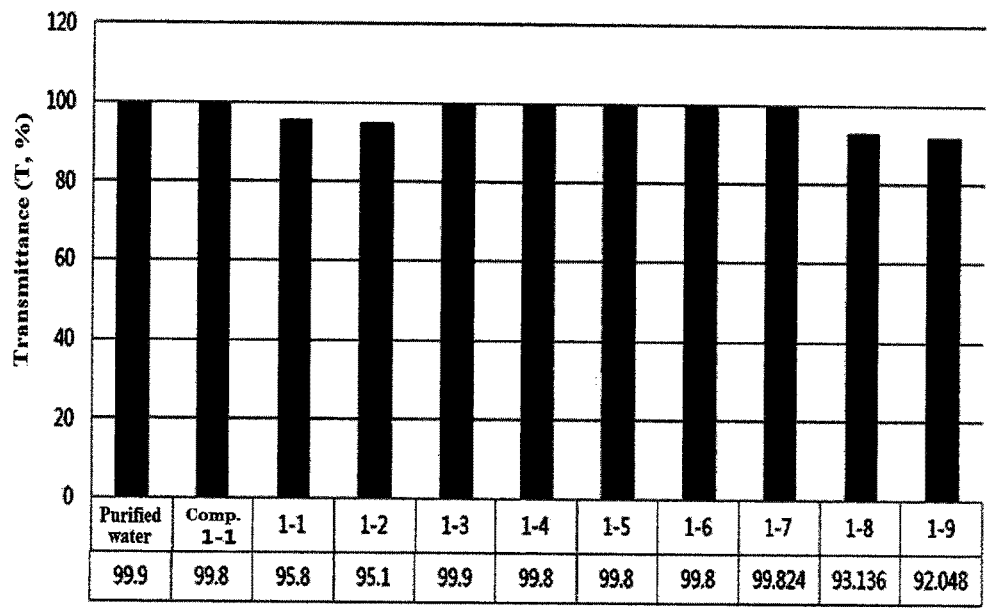
FIG. 4 shows the transmittance values of solubilization products containing different amounts of a heteropolysaccharide, which were prepared in Example 2.

The turbidity and transmittance values of the lotions (solubilization products) of Example 2, which were prepared using the ceramide-containing compositions of Example 1, are shown in FIGS. 3 and 4, respectively. As can be seen from the results in FIGS. 3 and 4, the solubilization product prepared using the composition of Example 1-3 had the highest transparency.

EXPERIMENTAL EXAMPLE 3

Evaluation of Images of the Solubilization Products Prepared in Example 2

Figure 5:
FIG. 5 shows images of solubilization products prepared in Example 2.
Figure 6:
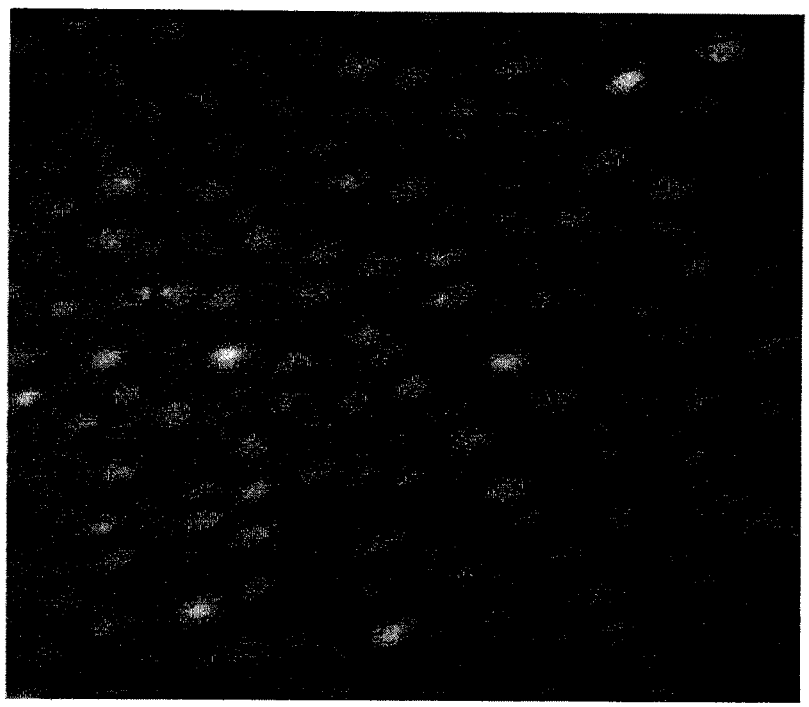
FIG. 6 shows a transmission electron image of a solubilization product including a composition prepared in Example 1-3.

FIG. 5 shows images of some solubilization products of Example 2, which were prepared using the compositions of Example 1. The visual observation confirmed that the compositions of Examples 1-3 and 1-7, each of which included 1-5% of the heteropolysaccharide, were highly transparent. FIG. 6 shows a transmission electron microscopy (TEM) image of the solubilization product including the composition of Example 1-3. The image of FIG. 6 reveals uniform distribution of the ceramide particles.

EXPERIMENTAL EXAMPLE 4

Analysis and Evaluation of Particle Sizes of the Solubilization Products Prepared in Example 2

The particle size of the solubilization product of Example 2, which was prepared using the composition of Example 1-3, was analyzed.

The difference in the transparency of an emulsion or solubilization system depending on the size of particles in the system is associated with the cut-off wavelength of visible light. When the size of micelles formed by emulsification or solubilization is larger than the cut-off wavelength of visible light, the micelles scatter visible light, and as a result, the system is colored ivory-white. Meanwhile, when the size of the micelles is smaller than the cut-off wavelength of visible light, the micelles do not scatter visible light, and as a result, the system becomes transparent.

Generally, micelles whose size is equal to or larger than the cut-off wavelength (780-380 nm) of visible light scatter incident visible light to produce an ivory-white color. In contrast, as the particle size decreases, a difference arises in the degree of scattering of visible light depending on the particle size, causing changes in appearance. The changes in appearance caused by the difference in the degree of scattering of visible light depending on the particle size are shown in Table 5.

TABLE 5

Changes in appearance depending on particle size

| Visual inspection | Particle size |
|---|---|
| Ivory-white | >1 μm (1000 nm) |
| Blue-white | 0.1 μm (100 nm)-1 μm (1000 nm) |
| Translucent | 0.05 μm (50 nm)-0.1 μm (100 nm) |
| Transparent | <0.05 μm (50 nm) |

The average size of the particles present in the solubilization product including the composition of Comparative Example 1-1 was 13.4 nm, as evaluated using a particle size analyzer (OTSUKA ELECTRONICS). The particles present in the solubilization product including the composition of Comparative Example 1-1 were found to have an average size of 12.9 nm. These results show that the solubilized ceramide micelle particles had a size not greater than the cut-off wavelength of visible light and were visually transparent, indicating that the addition of the heteropolysaccharide leads to an increase in transparency.

EXPERIMENTAL EXAMPLE 5

Evaluation of Zeta Potential of the Solubilization Product Prepared in Example 2

The zeta potential of the solubilization product of Example 2, which was prepared using the composition of Example 1-3, was measured.

Particles dispersed in a solution are electrically negatively or positively charged by the dissociation of surface polar groups and the adsorption of ions. To neutralize the interfacial charge, excess oppositely charged ions and a small amount of ions having the same polarity are diffusely distributed around the particles. As a result, an electric double layer is formed. The electric double layer is divided into two regions at the interface by a plane (the Stern plane) located at about a hydrated ion radius. The inner and outer regions divided by the Stern plane are defined as the Stern layer and the diffuse layer, respectively. A solution in which cations and anions are balanced accounts for most of the outer layer.

Generally, zeta potential refers to the potential in a slip plane close to the interface between an immobile layer and a diffuse layer. Since it is difficult to directly measure the surface potential of particles, information on the surface potential is generally discussed by a zeta potential value obtained mainly by an electrophoresis experiment. When all dispersed particles have zeta potentials of the same polarity (i.e. they are either highly negatively or positively charged), they are not bound to each other, they show a strong tendency to repulse each other and do not likely to be bound to each other. The criterion for the stability or instability of empirically determined zeta potential is +30 mV or −30 mV. As the absolute value of empirically determined zeta potential increases, the repulsive force between the particles increases, resulting in high stability of the particles.

Meanwhile, as the zeta potential approaches 0, the particles are likely to aggregate. For these reasons, zeta potential can be used as a measure of the stability of colloidal particles.

The solubilization products including the compositions of Comparative Example 1-1 and Example 1-2 were found to have zeta potentials of −37.42 mV and −39.74 mV, respectively, as measured using a zeta-potential analyzer (OTSUKA ELECTRONICS). These results show that the particles were prevented from aggregating by the repulsive force between the solubilized ceramide particles and were highly stable. Particularly, the mixing of the mannosylerythritol lipid and the heteropolysaccharide ensured uniform distribution of the ceramide particles.

EXAMPLE 3

Preparation of Solubilization Compositions Containing Different Amounts of the Mannosylerythritol Lipid Compositions were prepared in the same manner as in Example 1-3, except that the content of the mannosylerythritol lipid was changed as shown in Table 6. Changes in the transparency of the compositions with varying mannosylerythritol lipid contents were investigated.

TABLE 6

Compositions of Example 3

| Component (g) | 3-1 | 3-2 | 3-3 | 3-4 | 3-5 | 3-6 |
|---|---|---|---|---|---|---|
| Ceramide | 20 | 20 | 20 | 20 | 20 | 20 |
| Mannosylerythritol lipid | 5 | 10 | 15 | 20 | 25 | 30 |
| Polyoxyethylene (EO = 40) hydrogenated castor oil | 45 | 40 | 35 | 30 | 25 | 20 |
| Butylene glycol | 19 | 19 | 19 | 19 | 19 | 19 |
| Dipropylene glycol | 5 | 5 | 5 | 5 | 5 | 5 |
| Propylene glycol | 5 | 5 | 5 | 5 | 5 | 5 |
| Heteropolysaccharide | 1 | 1 | 1 | 1 | 1 | 1 |

EXAMPLE 4

Preparation of Solubilization Products Including the Solubilization Compositions of Example 3

Purified water was added to the compositions of Example 3, which included different amounts of the mannosylerythritol lipid, to prepare final products in which the ceramide was solubilized. The ceramide-containing solubilization products were prepared according to the same procedure as in Example 2.

EXPERIMENTAL EXAMPLE 6

Evaluation of Turbidities and Transmittances of the Compositions Prepared in Example 3

The transparency of the solubilization products of Example 4, which were prepared using the ceramide-containing compositions of Example 3, was evaluated according to the same procedure as in Experimental Example 2.

Figure 7:
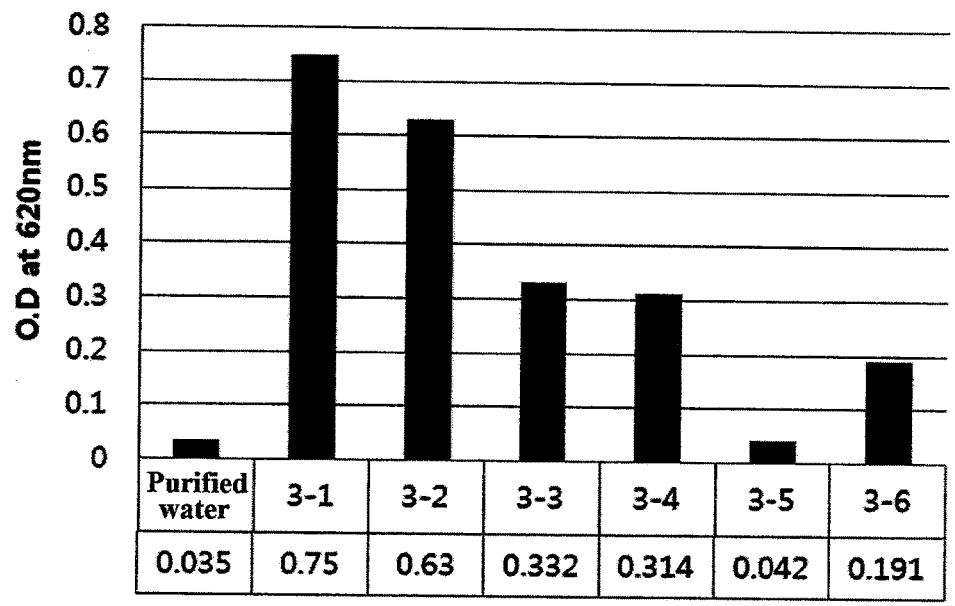
FIG. 7 shows the turbidity values of solubilization products containing different amounts of a mannosylerythritol lipid, which were prepared in Example 4.
Figure 8:
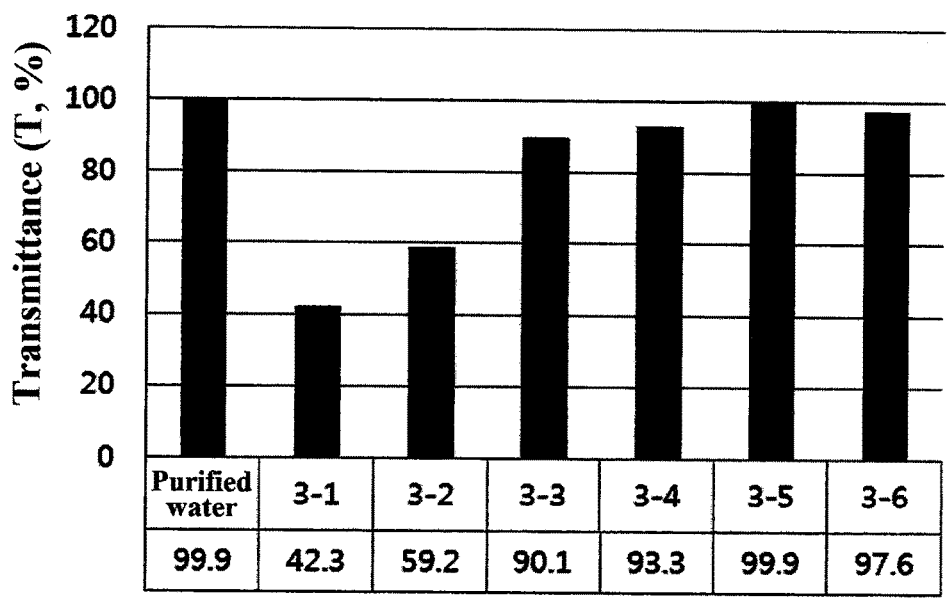
FIG. 8 shows the transmittance values of solubilization products containing different amounts of a mannosylerythritol lipid, which were prepared in Example 4.

The turbidity and transmittance values of the solubilization products of Example 4, which were prepared using the ceramide-containing compositions of Example 3, are shown in FIGS. 7 and 8, respectively. As can be seen from the results in FIGS. 7 and 8, the solubilization product prepared using the composition of Example 3-5, which included 15-30 wt % (about 25 wt %) of the mannosylerythritol lipid, had the highest transparency.

EXAMPLE 5

Preparation of Solubilization Compositions Containing Different Kinds of Poorly Soluble Substances Compositions including poorly soluble substances as active ingredients were prepared as shown in Table 7. The compositions were prepared according to the same procedure as in Example 1.

TABLE 7

Compositions of Example 5

| Component (g) | 5-1 | 5-2 | 5-3 | 5-4 | 5-5 | 5-6 | 5-7 | 5-8 | 5-9 | 5-10 | 5-11 |
|---|---|---|---|---|---|---|---|---|---|---|---|
| Ceramide | 20 | | | | | | | | | | |
| Rutein | | 20 | | | | | | | | | |
| Resveratrol | | | 20 | | | | | | | | |
| Phylloquinone | | | | 20 | | | | | | | |
| Ubiquinone | | | | | 20 | | | | | | |
| Oleanolic acid | | | | | | 20 | | | | | |
| Bis-ethylhexyloxyphenol methoxyphenyl triazine | | | | | | | 20 | | | | |
| Astaxanthin | | | | | | | | 20 | | | |
| Rutin | | | | | | | | | 20 | | |
| Hesperidin | | | | | | | | | | 20 | |
| Chloramphenicol | | | | | | | | | | | 20 |
| Mannosylerythritol lipid | 25 | 25 | 25 | 25 | 25 | 25 | 25 | 25 | 25 | 25 | 25 |
| Polyoxyethylene (EO = 40) hydrogenated castor oil | 25 | 25 | 25 | 25 | 25 | 25 | 25 | 25 | 25 | 25 | 25 |
| Butylene glycol | 19 | 19 | 19 | 19 | 19 | 19 | 19 | 19 | 19 | 19 | 19 |
| Dipropylene glycol | 5 | 5 | 5 | 5 | 5 | 5 | 5 | 5 | 5 | 5 | 5 |
| Propylene glycol | 5 | 5 | 5 | 5 | 5 | 5 | 5 | 5 | 5 | 5 | 5 |
| Heteropolysaccharide | 1 | 1 | 1 | 1 | 1 | 1 | 1 | 1 | 1 | 1 | 1 |

EXAMPLE 6

Preparation of Solubilization Products Including the Solubilization Compositions of Example 5

Purified water was added to the compositions of Example 5, which included different kinds of poorly soluble substances, to prepare final solubilization products. The solubilization products were prepared according to the same procedure as in Example 2.

EXPERIMENTAL EXAMPLE 7

Figure 9:
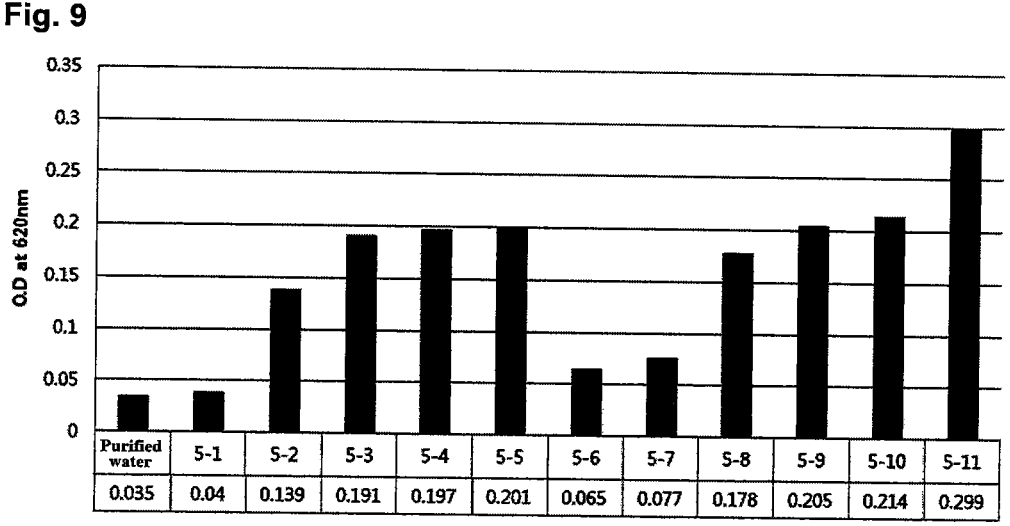
FIG. 9 shows the turbidity values of solubilization products containing different kinds of poorly soluble substances, which were prepared in Example 6.
Figure 10:
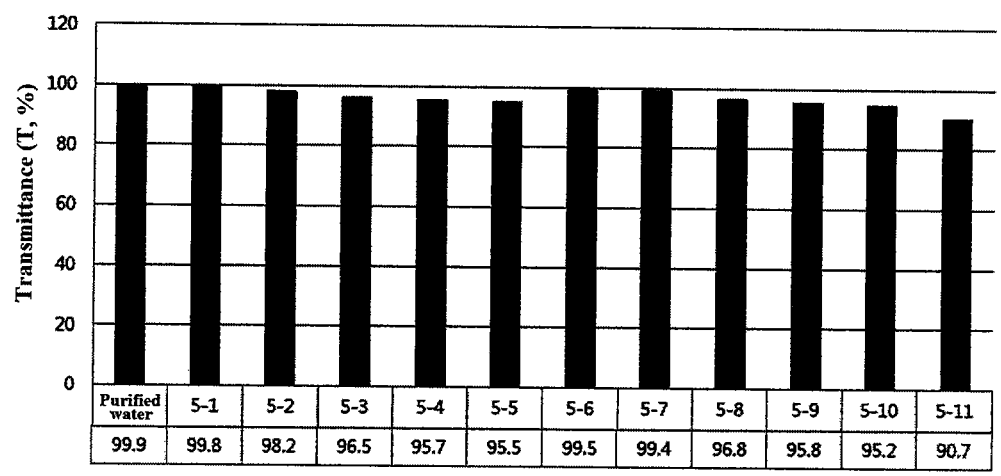
FIG. 10 shows the transmittance values of solubilization products containing different kinds of poorly soluble substances, which were prepared in Example 6.

Evaluation of Turbidities and Transmittances of the Compositions Including Different Kinds of Poorly Soluble Substances The turbidity and transmittance values of the solubilization products of Example 6 in which the excess poorly soluble substances were solubilized are shown in FIGS. 9 and 10, respectively.

As can be seen from the results in FIGS. 9 and 10, the composition and the method of the present invention can solubilize various poorly soluble hydrophobic substances, including ceramide, resveratrol, phylloquinone, ubiquinone, oleanolic acid, bis-ethylhexyloxyphenol triazine, astaxanthin, rutin, hesperidin, and chloramphenicol, compared to conventional solubilization compositions and methods.

While the present invention has been described herein with reference to its specific embodiments, these embodiments do not serve to limit the composition and method of the present invention and those skilled in the art will appreciate that various modifications and improvements can be made thereto without departing from the spirit and scope of the present invention. Simple modifications and variations of the present invention belong to the scope of the present invention and the specific scope of the present invention will be clearly defined by the appended claims.

As is apparent from the foregoing, the composition and the method of the present invention are effective in solubilizing poorly soluble substances that are known to have good activities but have limited large-scale applications.

In addition, the composition and the method of the present invention efficiently improve the solubilization of various kinds of poorly soluble substances, which have previously been difficult to solubilize, so that the effects of final products containing the substances can be maximized.

What is claimed is:

1. A composition for solubilizing a substance in water, comprising a combination of:
   (a) a mannosylerythritol lipid;
   (b) a heteropolysaccharide;
   (c) a surfactant; and
   (d) a polyol,
wherein the combination forms an organic solution and wherein the composition comprises 100 parts by weight of the mannosylerythritol lipid, 0.1 to 100 parts by weight of the heteropolysaccharide containing galactose, glucose, and mannose units, 10 to 4500 parts by weight of the surfactant, and 10 to 3000 parts by weight of the polyol.

2. The composition according to claim 1, wherein the mannosylerythritol lipid is represented by Formula 1:

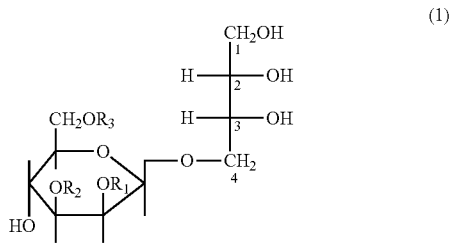

(1)

wherein $R_1$ and $R_2$ are identical to or different from each other and are each independently a $C_6$-, $C_{12}$- or $C_{14}$-chain saturated or unsaturated fatty acid and $R_3$ is an acetyl group.

3. The composition according to claim 1, wherein the heteropolysaccharide contains galactose, glucose, and mannose units in a molar ratio of 1-3:3-6:1-3.

4. The composition according to claim 1, wherein the heteropolysaccharide is produced from *Candida* sp.

5. The composition according to claim 1 comprising a first heteropolysaccharide having a molecular weight of 50000 to 80000 daltons, a second heteropolysaccharide having a molecular weight of 20000 to 50000 daltons, a third heteropolysaccharide having a molecular weight of 5000 to 20000 daltons, a fourth polysaccharide having a molecular weight of 140000 to 160000 daltons, and a fifth polysaccharide having a molecular weight of 160000 to 180000 daltons.

6. The composition according to claim 1, wherein the surfactant is selected from polyoxyethylene hydrogenated castor oil, Ceteareth, Ceteth, Glycereth, Laureth, Oleth, Polysorbates, Steareth, amino acid-fatty acid esters, polyoxyethylene stearate, and mixtures thereof.

7. The composition according to claim 1, wherein the polyol is selected from butylene glycol, dipropylene glycol, propylene glycol, caprylyl glycol, decylene glycol, ethylene glycol, hexylene glycol, polyethylene glycol, glycerin, diglycerin, ethylhexylglycerin, polyglycerin, 1,6-hexanediol, 1,2-hexanediol, 1,2-octanediol, and mixtures thereof.

8. The composition according to claim 1, further comprising a substance selected from ceramide, rutein, resveratrol, phylloquinone, ubiquinone, oleanolic acid, bis-ethylhexyloxyphenol methoxyphenyl triazine, astaxanthin, rutin, hesperidin, chloramphenicol, and mixtures thereof that are used in a cosmetic or pharmaceutical composition.

9. A method for solubilizing a substance in water, comprising:
   (i) sequentially mixing a mannosylerythritol lipid, a selected substance for delivery, a heteropolysaccharide, a surfactant, and a polyol, wherein the composition comprises 100 parts by weight of the mannosylerythritol lipid, 0.1 to 100 parts by weight of the heteropolysaccharide containing galactose, glucose, and mannose units, 10 to 4500 parts by weight of the surfactant, and 10 to 3000 parts by weight of the polyol; and
   (ii) heating and stirring the mixture to form an organic solution.

10. The method according to claim 9, wherein the mixture comprises 100 parts by weight of the mannosylerythritol lipid, 2 to 4000 parts by weight of the selected substance, 0.1 to 100 parts by weight of the heteropolysaccharide containing galactose, glucose, and mannose units, 10 to 4500 parts by weight of the surfactant, and 10 to 3000 parts by weight of the polyol.

11. The method according to claim 9, wherein the mannosylerythritol lipid is represented by Formula 1:

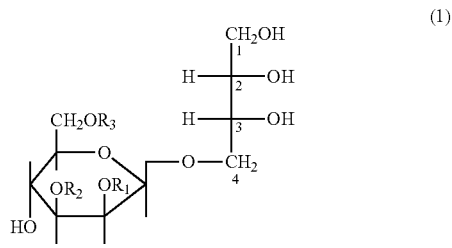

(1)

wherein $R_1$ and $R_2$ are identical to or different from each other and are each independently a $C_6$-, $C_{12}$- or $C_{14}$-chain saturated or unsaturated fatty acid and $R_3$ is an acetyl group.

12. The method according to claim 9, wherein the heteropolysaccharide contains galactose, glucose, and mannose units in a molar ratio of 1-3:3-6:1-3.

13. The method according to claim 9, wherein the heteropolysaccharide is produced from *Candida* sp.

14. The method according to claim 9, wherein the composition comprises a first heteropolysaccharide having a molecular weight of 50000 to 80000 daltons, a second heteropolysaccharide having a molecular weight of 20000 to 50000 daltons, a third heteropolysaccharide having a molecular weight of 5000 to 20000 daltons, a fourth polysaccharide having a molecular weight of 140000 to 160000 daltons, and a fifth polysaccharide having a molecular weight of 160000 to 180000 daltons.

15. The method according to claim 9, wherein the composition comprises polyoxyethylene hydrogenated castor oil, Ceteareth, Ceteth, Glycereth, Laureth, Oleth, Polysorbates, Steareth, amino acid-fatty acid esters, polyoxyethylene stearate, or mixtures thereof.

16. The method according to claim 9, wherein the polyol is selected from butylene glycol, dipropylene glycol, propylene glycol, caprylyl glycol, decylene glycol, ethylene glycol, hexylene glycol, polyethylene glycol, glycerin, diglycerin, ethylhexylglycerin, polyglycerin, 1,6-hexanediol, 1,2-hexanediol, 1,2-octanediol, and mixtures thereof.

17. The method according to claim 9, wherein the selected substance is selected from ceramide, rutein, resveratrol, phylloquinone, ubiquinone, oleanolic acid, bis-ethylhexyloxyphenol methoxyphenyl triazine, astaxanthin, rutin, hesperidin, chloramphenicol, and mixtures thereof that are used in a cosmetic or pharmaceutical composition.

18. The method according to claim 9, wherein the heating temperature is from 40 to 80° C.

* * * * *

UNITED STATES PATENT AND TRADEMARK OFFICE
CERTIFICATE OF CORRECTION

PATENT NO. : 10,226,413 B2
APPLICATION NO. : 15/033021
DATED : March 12, 2019
INVENTOR(S) : Kwang-Nyeon Kim, Ju-Hyun Son and Hee-Sik Kim Page 1 of 1

It is certified that error appears in the above-identified patent and that said Letters Patent is hereby corrected as shown below:

On the Title Page

Column 1, item (73), in "Assignees", Line 1-Line 4, delete "DAMY CHEMICAL CO., LTD., Seoul (KR); KOREA RESEARCH INSTITUTE OF BIOSCIENCE AND BIOTECHNOLOGY" insert -- DKBIO CO., LTD. --, therefor.

Signed and Sealed this
Twenty-fifth Day of February, 2020

Andrei Iancu
*Director of the United States Patent and Trademark Office*